(12) United States Patent
Williams

(10) Patent No.: US 11,123,148 B2
(45) Date of Patent: Sep. 21, 2021

(54) COORDINATED SIZER-PUNCH TOOL FOR ARTICULAR CARTILAGE REPAIR

(71) Applicant: Riley Williams, New York, NY (US)

(72) Inventor: Riley Williams, New York, NY (US)

( * ) Notice: Subject to any disclaimer, the term of this patent is extended or adjusted under 35 U.S.C. 154(b) by 266 days.

(21) Appl. No.: 16/341,370

(22) PCT Filed: Oct. 16, 2017

(86) PCT No.: PCT/US2017/056721
§ 371 (c)(1),
(2) Date: Apr. 11, 2019

(87) PCT Pub. No.: WO2018/071888
PCT Pub. Date: Apr. 19, 2018

(65) Prior Publication Data
US 2020/0046447 A1    Feb. 13, 2020

Related U.S. Application Data

(60) Provisional application No. 62/408,092, filed on Oct. 14, 2016.

(51) Int. Cl.
| A61B 17/16 | (2006.01) |
| A61B 90/00 | (2016.01) |
| A61F 2/30 | (2006.01) |
| A61F 2/46 | (2006.01) |

(Continued)

(52) U.S. Cl.
CPC .......... *A61B 90/06* (2016.02); *A61B 17/1604* (2013.01); *A61F 2/30756* (2013.01);
(Continued)

(58) Field of Classification Search
CPC ............ A61F 2002/30756; A61F 2002/30757; A61F 2002/30761; A61F 2002/30762;
(Continued)

(56) References Cited

U.S. PATENT DOCUMENTS 5,919,196 A    7/1999  Bobic et al.
5,954,671 A *  9/1999  O'Neill .............. A61B 17/1635
                                                      600/567

(Continued)

FOREIGN PATENT DOCUMENTS

| EP | 2389904 A1 | 11/2011 |
| EP | 2389904 B1 | 11/2011 |
| EP | 2564792 A1 | 3/2013 |

OTHER PUBLICATIONS

P. Ho et al., "Arthroscopic Osteochondral Grafting for Radiocarpal Joint Defects", Journal of Wrist Surgery vol. 2, No. Mar. 2013, pp. 212-219 (2013).

(Continued)

*Primary Examiner* — Samuel S Hanna
(74) *Attorney, Agent, or Firm* — Weitzman Law Offices, LLC

(57) ABSTRACT

A tool system for the repair of joint articular cartilage defects is disclosed. The tool system may include a non-trephine cutting tool, having a handle coupled to a movable support and a cutter section, coupled to the handle. The cutter section has a closed geometric peripheral shape sized to surround a lesion in cartilage of an articular joint. The cutter section also has a cutting edge that is sufficiently sharp to cut, by the application of force normal to the cutting edge, through cartilage surrounding a joint articular cartilage lesion from a repair site while having insubstantial effect on subchondral bone underlying the cartilage surrounding the joint articular cartilage lesion cartilage being cut, and a cartilage repair patch.

15 Claims, 6 Drawing Sheets

(51) Int. Cl.
*A61B 50/30* (2016.01)
*A61B 17/00* (2006.01)

(52) U.S. Cl.
CPC ........ *A61F 2/4618* (2013.01); *A61B 50/3001* (2016.02); *A61B 2017/0046* (2013.01); *A61B 2017/00907* (2013.01); *A61B 2090/034* (2016.02); *A61B 2090/061* (2016.02); *A61B 2090/3916* (2016.02); *A61B 2090/3937* (2016.02)

(58) Field of Classification Search
CPC ............ A61F 2002/30764; A61F 2002/30766; A61F 2/4618; A61B 17/1604; A61B 17/1635; A61B 17/1675; A61B 17/1637
See application file for complete search history.

(56) References Cited

U.S. PATENT DOCUMENTS

| | | | |
|---|---|---|---|
| 9,216,022 B2 | 12/2015 | Karnes et al. | |
| 9,421,082 B2 | 8/2016 | Sengun et al. | |
| 2004/0059425 A1 | 3/2004 | Schmieding | |
| 2006/0178748 A1* | 8/2006 | Dinger | A61F 2/28 623/18.11 |
| 2006/0235419 A1 | 10/2006 | Steinwachs et al. | |
| 2009/0299371 A1 | 12/2009 | Steiner et al. | |
| 2012/0150030 A1 | 6/2012 | Reach et al. | |
| 2013/0197666 A1 | 8/2013 | Segun et al. | |
| 2014/0276231 A1* | 9/2014 | Wood | A61B 17/3205 600/587 |
| 2015/0150030 A1 | 5/2015 | Ku et al. | |

OTHER PUBLICATIONS

G. Gorniak, "Patterns of Patellofemoral Articular Cartilage Wear in Cadavers", Journa of Orthopaedic & Sports Physical Therapy, vol. 39, No. 9, pp. 675-683 (Sep. 2009).

E. Solheim et al., "Osteochondral autgrafting (mosaicplasty) in articular cartilage defects in the knee: Results at 5 to 9 years", The Knee 17, pp. 84-87 (2010).

International Search Report for International (PCT) Application No. PCT/US2017/056721 (dated Dec. 21, 2017).

\* cited by examiner

COORDINATED SIZER-PUNCH TOOL FOR ARTICULAR CARTILAGE REPAIR

CROSS-REFERENCE TO RELATED APPLICATIONS

This application claims the priority benefit of U.S. Provisional Patent Application Ser. No. 62/408,092 filed Oct. 14, 2016, the entirety of which is incorporated herein by reference.

TECHNICAL FIELD

This disclosure relates to the repair of human cartilage defects, and more particularly, to the repair of joint articular cartilage defects.

BACKGROUND

Articular cartilage has a limited capacity for repair. As such, surgical manipulation of symptomatic lesions of the knee, shoulder, elbow, or hip are necessary to effectively repair these cartilage defects.

One approach to repairing cartilage defects is osteochondral grafting, which uses a trephine (a type of round hole saw) to remove one or more cores of defect-containing cartilage along with a portion of the underlying bone and then takes one or more plugs of cartilage and underlying bone without any defect(s) from another location, or from a donor joint, and transfers the plug(s) to the site where the defect-containing cartilage and bone were removed. However, donor grafts are not always readily available and there is always the real possibility that the donor cartilage will fail to integrate completely with the existing cartilage, potentially leading to the need for a joint replacement or creating problems in the donor site joint, after donor cartilage removal.

Autologous chondrocyte implantation (ACI) is another method that has been used for the repair of cartilage defects since the 1990s. Unfortunately, the clinical results of this methodology were highly variable, and the technique difficult to execute. As a result, there has been a concerted effort by surgeons and industry to improve upon this method by adding a collagen base patch or hydrogel to the ACI method.

In this updated ACI methodology, a patient's cells are harvested from the affected joint (e.g., knee) and expanded in culture. Following cellular expansion, the patient's cartilage cells are seeded onto a scaffold or matrix that is typically made of collagen or other cartilage-based proteins. This newly formed "patch" is then re-implanted into the patient as a means of replacing cartilage in areas where it has worn away.

There are some hydrogel implants that do not include cells, but these patches still contain many of the same articular cartilage subcomponents (e.g., collagen, proteoglycans, water). These acellular scaffolds are also useful for cartilage repair and generally have mechanical properties that are identical to the modified ACI patches described above. In addition to collagen and cells, these hydrogel implants are highly hydrated and tend to be very slippery. Moreover, seeded collagen patches are usually shipped to operating surgeons in a nutritive medium.

For purposes of this application, as used herein, the term "cartilage repair patch" means, and is intended to encompass, patches of cartilage cells seeded onto a scaffold or matrix, hydrogel implants, and other materials used to replace cartilage lesions in the repair of joint articular cartilage.

During the process of surgically repairing a lesion in articular cartilage of a joint, the surgeon must typically:
1. Identify the cartilage lesion (i.e., joint cartilage defect);
2. Size and shape the host joint defect;
3. Shape and fashion a patch to match the host joint defect it will replace; and
4. Implant and secure the patch at the location of host joint defect.

Unfortunately, due to patch slipperiness and/or the medium in which some patches are shipped, handling the patches described above is very difficult using the instruments and tools typically available to orthopedic surgeons (e.g., knives, forceps, retractors, scissors, etc.). This makes the process of shaping and fashioning the patch even more difficult, often leading to damage and waste of patch material.

Accordingly, there is a need for a system, method and medical devices that will allow surgeons to better identify and size an articular cartilage lesion, and create an appropriately sized cartilage repair patch. In addition, there is also a need for improved medical devices and methods that ease creation and implantation of cartilage repair patches, while decreasing the likelihood of damage and waste.

SUMMARY

I have devised various devices and kits that solve one or more of the foregoing problems by allowing surgeons and other medical professionals to easily and efficiently prepare a cartilage lesion site by and corresponding patch.

One aspect involves a system for use in repairing joint articular cartilage lesions. The system involves a first non-trephine cutting tool and a second non-trephine cutting tool, each having a closed geometric peripheral shape, wherein the peripheral shape of the first non-trephine cutting tool is different from the second non-trephine cutting tool in at least one of a size, a geometric peripheral shape, or a curvature of a cutting edge, and the cutting edge is sufficiently sharp to cut, by the application of force normal to the cutting edge, through a) cartilage surrounding a joint articular cartilage lesion from a repair site while having insubstantial effect on subchondral bone underlying the cartilage surrounding the joint articular cartilage lesion cartilage being cut, and b) a cartilage repair patch. The system further includes at least two lesion sizing elements, a first of the at least two lesion sizing elements having a first site marking feature that allows for placement of registration markings on cartilage surrounding a joint articular cartilage lesion for the first cutting tool, and a second of the at least two lesion sizing elements having a second site marking feature that allows for placement of registration markings on cartilage surrounding a joint articular cartilage lesion for the second cutting tool, as well as a repair patch support, associated with one of the first or second cutting tool, which will support a specific cartilage repair patch that was cut using the one of the first or second cutting tool, and will assist in one or more of transfer to the repair site, or proper placement at the repair site, of a specific cartilage repair patch cut using the one of the first or second cutting tool.

Another aspect of the invention involves a tool for use in joint articular cartilage repair. The tool involves a non-trephine cutting tool, having i) a handle coupled to a movable support; and ii) a cutter section, coupled to the handle, the cutter section having a closed geometric peripheral shape sized to surround a lesion in cartilage of an articular joint, the cutter section having a cutting edge that is sufficiently sharp to cut, by the application of force normal to the cutting edge, through a) cartilage surrounding a joint articular cartilage lesion from a repair site while having insubstantial effect on subchondral bone underlying the cartilage surrounding the joint articular cartilage lesion cartilage being cut, and b) a cartilage repair patch. The movable support has a peripheral shape that fits within, and closely corresponds to, the closed geometric peripheral shape of the cutter section.

DETAILED DESCRIPTION

With less invasive procedures than osteochondral grafting, as noted above, the standard practice in repairing a joint articular cartilage lesion is to remove the cartilage that contains, and some that surrounds, the lesion, and then produce a corresponding patch that matches the area where the lesion was removed. However, as also noted, current practice is difficult, as it requires the surgeon to skillfully handle and accurately cut the patch material, on an ad hoc basis, to a size and shape that conforms to the area where the lesion was removed. This results in risk of damage to the patch material and/or waste because, as noted above, common surgical tools are largely ill-suited for handling the patch materials.

I have devised various device variants and kits that solve one or more of the foregoing problems by allowing surgeons and other medical professionals to easily and efficiently prepare a cartilage lesion site for a patch containing lesion-containing cartilage for removal (without removing a core or plug of bone using a trephine, as is done in osteochondral grafting) while having trivial-to-no removal of, or adverse effect on, the subchondral bone underlying that cartilage, and to then accurately form a patch that matches the size and shape of the site from which the cartilage was removed.

Figure 1:
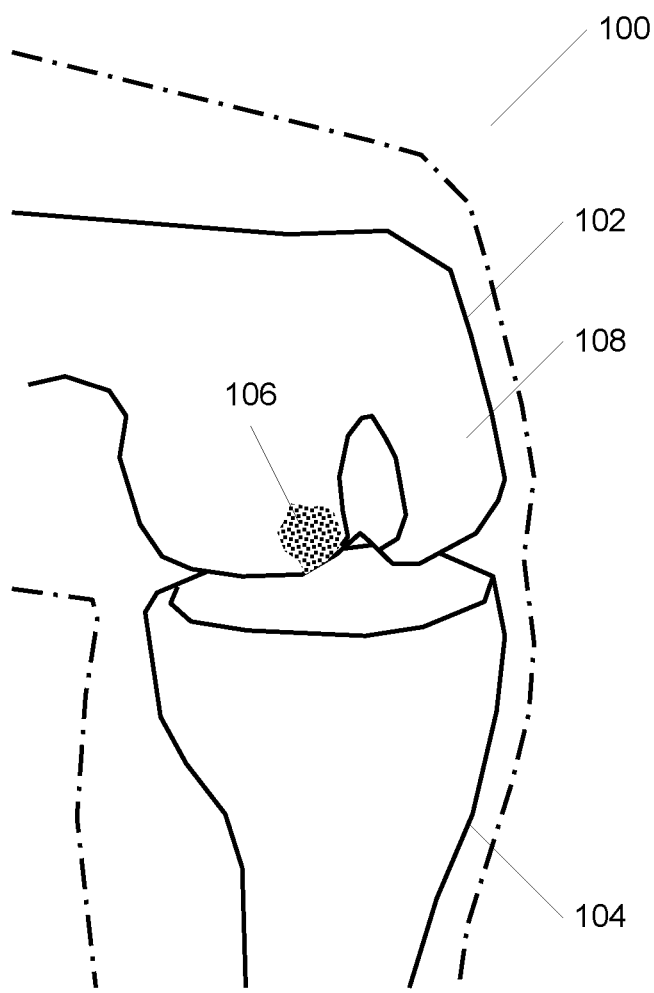
FIG. 1 illustrates, in simplified form, a leg and interior bones of a knee joint.

FIG. 1 illustrates, in simplified form, a leg 100 and interior bones, a femur 102 and tibia 104 of a knee joint (for simplicity, patella and fibula not shown), where the femur 102 has a cartilage lesion 106 on part of its articular surface 108.

Figure 2:
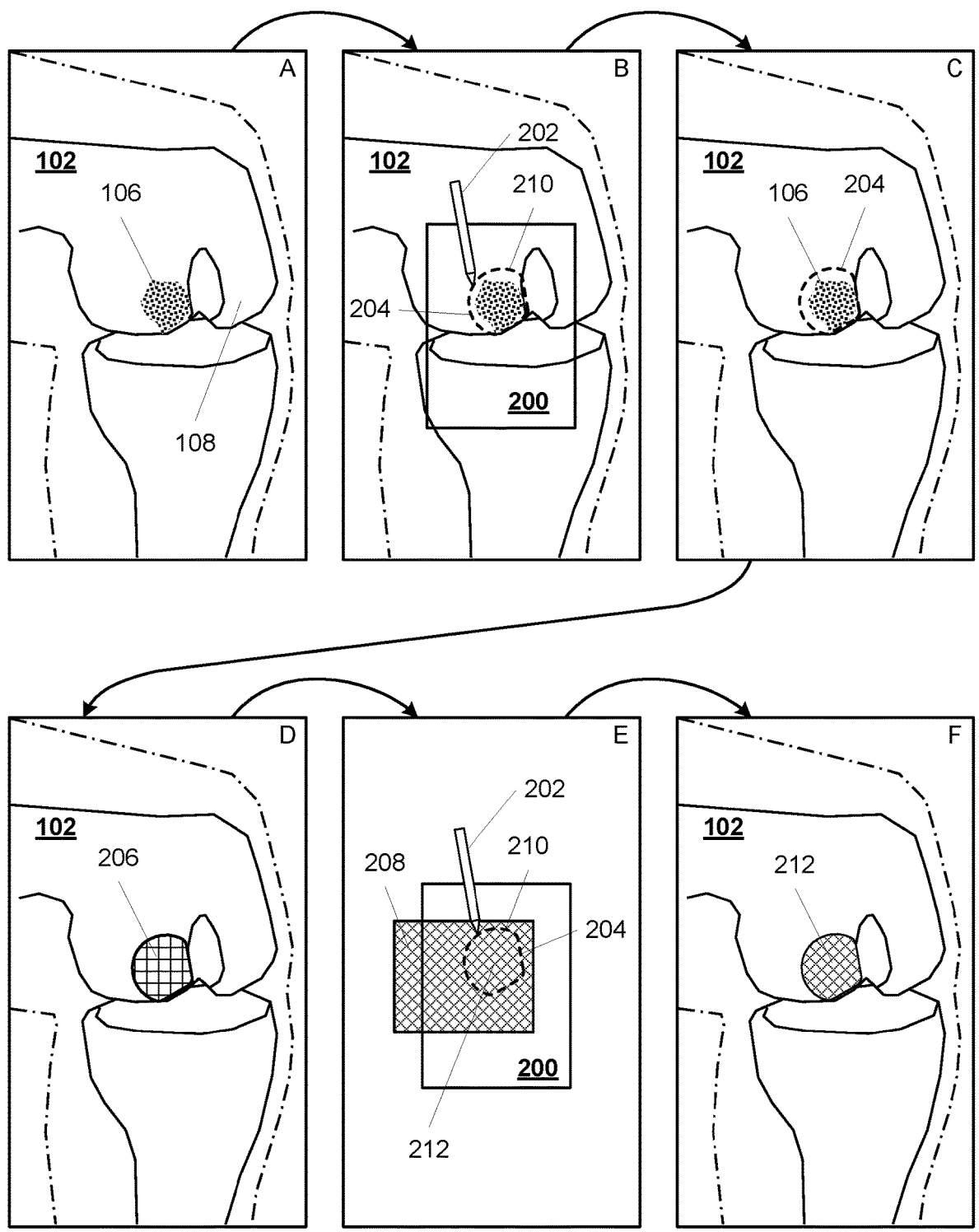
FIG. 2 illustrates, in simplified form, a portion of an example femur oriented to present its articular surface.

FIG. 2 illustrates, in simplified form, the process for using one example variant lesion sizer 200 to repair the cartilage lesion 106 on the articular surface 108 of the femur 102 of FIG. 1 (for simplicity, patella and fibula not shown).

Figure 3:
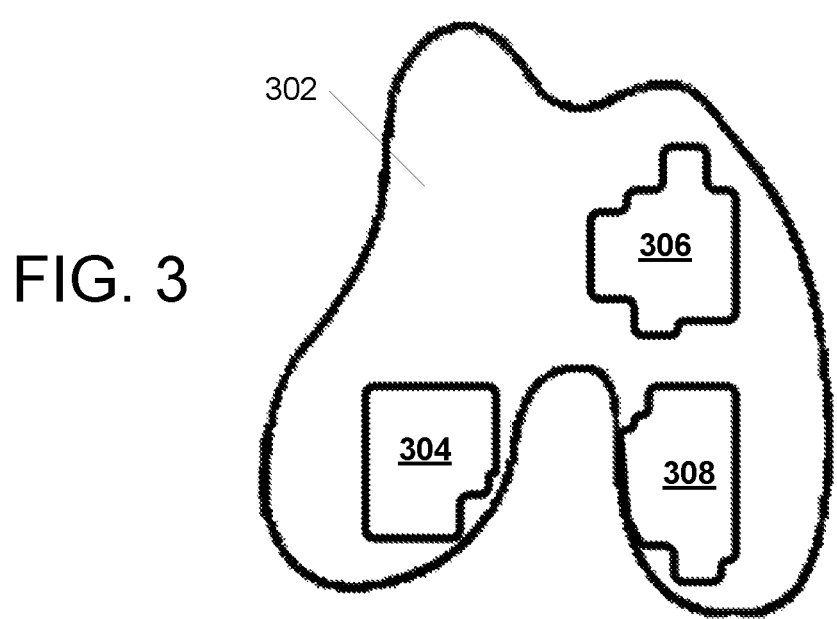
FIG. 3 illustrates, in simplified form, the process for using one example variant lesion sizer pad to repair the cartilage lesion on the articular surface of the femur of FIG. 1.

The example variant lesion sizer 200 used in connection with FIG. 3, is made from a material, and is of a thickness, that provides significant flexibility and/or deformability, but does not allow it to be not stretched, so that it can be flexed/deformed to conform to the shape of cartilage containing, and surrounding, the lesion to be repaired. For example, plastic or other appropriate material that can be sterilized for a single use can be used. The lesion sizer 200 material for this variant is ideally transparent or at least highly translucent, in whole or part, to enable the surgeon to place the lesion sizer 200 on top of the cartilage lesion and view the lesion through it.

Depending upon the particular implementation, the lesion sizer 200 of this type will have a series of holes and/or slots that form the periphery of at least one closed geometric shape and can be matched with, and used by the surgeon to mark the periphery of, the cartilage lesion 106 to be repaired on the cartilage surface and correspondingly mark the periphery of a repair patch that will replace the portion of cartilage containing the lesion 106.

FIG. 3 illustrates, in simplified form, a portion of an example femur 102 oriented to present its articular surface 302. As identified in Gorniak, "Patterns of Patellofemoral Articular Cartilage Wear in Cadavers", Journal of Orthopaedic & Sports Physical Therapy, Vol. 39, No. 9 (September 2009), there are roughly three regions 304, 306, 308 where cartilage wear lesions typically occur, in aggregate, in males and females, on the left and right knees. As such, some implementations of the lesion sizers and cutting tools (as described below) can be shaped and sized to take into account, or mimic, these regions and thereby standardize the cartilage area to be replaced, allowing for standard size and shaped repair patches to be formed. In this manner, the consistency is improved and surgical time can be reduced.

Figure 4:
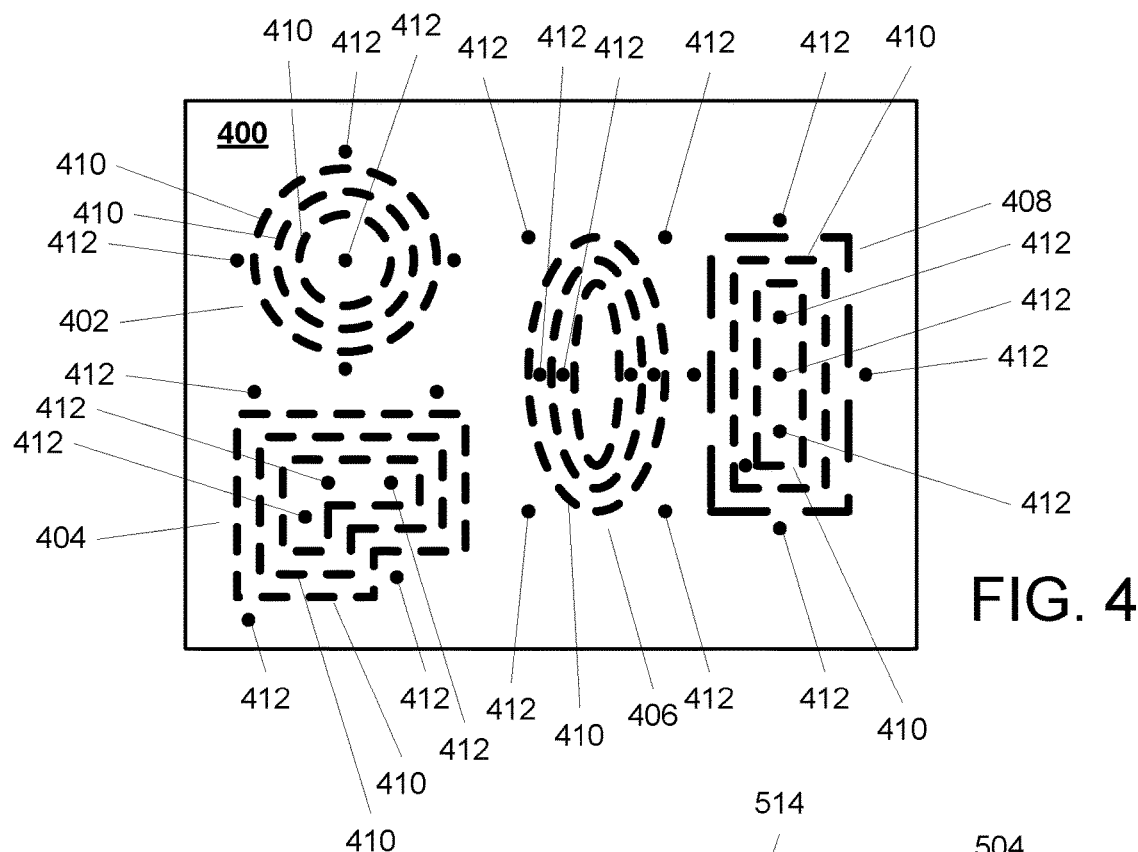
FIG. 4 illustrates, in simplified form, one example of a variant lesion sizer.

FIG. 4 illustrates, in simplified form, one example of a variant lesion sizer 400. As shown, this variant contains four sets 402, 404, 406, 408 of shapes, defined by a series of through-slots or holes 410 that can be used with a surgical marking pen to mark underlying material cartilage or repair patch material. The sets 402, 404, 406, 408 further include a series of registration openings 412 that can likewise be marked on cartilage to allow for use of combinations of the shapes to surround a particular lesion and, as will be discussed in greater detail below, can be used to assist with alignment and placement of one or more cutting tools and/or a repair patch.

In addition, as shown, each set 402, 404, 406, 408 made up of several different sized versions of such shapes, arranged as concentric versions of the same geometric shape so that the surgeon can select a size that will minimize the amount of healthy cartilage surrounding the cartilage lesion 106 that will be designated for removal if desired.

Returning to FIG. 2, as shown in Panel "A", the process starts with the identification of the lesion 106 to be repaired. Next, as shown in Panel "B", the slots and/or holes 210 of the lesion sizer 200 for a particular shape and size (only one of which is shown) is aligned with the lesion 106 and the periphery is marked 204 using the slots or holes 210 on the underlying cartilage with a surgical marker 202. Note here that the flexibility lesion sizer 200 ensures that the lesion sizer 200 can be closely conformed to the underlying cartilage shape. The lesion sizer 200 is then removed and, as shown in Panel "C", leaving the markings 204 about the lesion periphery visible on the cartilage of the articular surface 108. Next, the markings 204 are used to denote and guide where to cut the cartilage and, once the periphery of the cartilage is cut using the markings 204 as a guide, the lesion-containing cartilage can be removed in the conventional manner, for example, using a scalpel, cartilage curette or other appropriate tool, until all of the cartilage within the peripheral boundary has been removed down to the underlying subchondral bone 206 as shown in Panel "D". The same peripheral markings of the lesion sizer 200 that were used to denote the periphery of cartilage to be removed, are likewise used to apply corresponding markings onto the repair patch material 208 by placing the lesion sizer 200 on the repair patch material 206 and repeating the process used on the joint cartilage as shown in Panel "E" to define a repair patch 212 that corresponds to the prepared repair site. Note here that, because the lesion sizer 200 does not stretch, when flattened for use with the patch material 208, marking consistency will be maintained. The patch material 208 can then be cut, using the markings as a guide, to form the repair patch 212 thereby ensuring a close fit between the repair patch 212 and the repair site, as shown in Panel "F", thereby minimizing the handling and need for trimming the repair patch 212 for the corresponding repair site. As should be appreciated, through use of such a simple lesion sizer 200, much of the guesswork and complex contouring of a replacement patch can be avoided, thereby improving efficiency.

While the foregoing approach provides significant benefits and advantages, it still relies upon the surgeon's ability to consistently cut both the lesion-containing cartilage and the replacement patch. Advantageously, a further variant of my devices and approaches, addresses that issue and, thereby, provides additional benefits and advantages.

Figure 5:
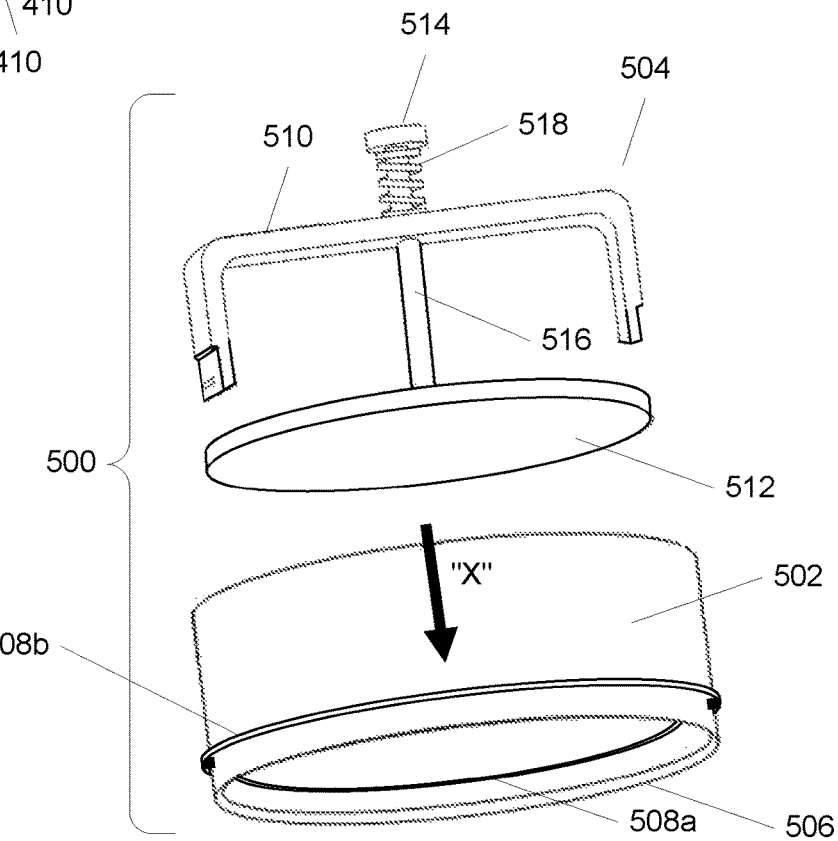
FIG. 5 illustrates, in simplified form, another example variant device, a non-trephine cutting tool.

FIG. 5 illustrates, in simplified form, another example variant device, a non-trephine cutting tool 500, that is usable with, for example, the lesion sizers 200, 400 described above, that provides for more consistent cutting of cartilage and a corresponding repair patch and, in addition, makes handling of a cut repair patch easier.

As shown, the non-trephine cutting tool 500 is made up of two parts, a cutter section 502 and a manipulator section 504.

The cutter section 502 is configured to form a closed geometric peripheral shape that corresponds in size to one of the shapes of a lesion sizer 200, 400. The cutter section 502 includes a cutting edge 506 that is sufficiently sharp enough to cut, by the application of force normal to the cutting edge (along arrow "X"), through: (a) cartilage surrounding a joint articular cartilage lesion from a repair site, while having insubstantial effect on subchondral bone underlying the cartilage surrounding the joint articular cartilage lesion cartilage being cut, and also (b) a cartilage repair patch. At this point it is to be understood that the reference to "insubstantial effect" is intended to mean that, although it may cut into or score subchondral bone tissue, it will not remove a plug of subchondral bone as a trephine would.

Optionally, the cutter section 502 may include one or more depth stop features, such as a lip or protrusion, as an interior depth stop 508a or as an exterior depth stop 508b for the cutter section 502, to help minimize cutting into subchondral bone tissue underlying the cartilage at the repair site. Depending upon the particular implementation and intended location for use, the optional depth stop will impede cutting into the subchondral bone (if at all) much beyond the cartilage thickness in the repair site (e.g., into the subchondral bone to a depth <0.4 mm or so). Thus, the depth stop feature will ideally take into account the thickness of the cartilage to be cut, plus some small amount to ensure reaching the subchondral bone. For purposes of completeness, cartilage thickness in the areas where lesions requiring repair commonly occur, is typically in the range of 0.94 mm to 1.63 mm for ankle cartilage, 1.69 mm to 2.65 mm for knee cartilage, 1.08 mm to 2.4 mm for hip cartilage and 0.89 mm to 2.88 mm for shoulder cartilage.

The manipulator section 504 is made up of a handle 510 and a moveable support 512 that is coupled to the handle 510 and can be manipulated by, for example, applying pressure to a cap 514 of a plunger shaft 516 and return spring 518 coupled to the handle 510. Depending upon the particular implementation, the handle 510 of the manipulator section 504 can be removably attachable to the cutter section 502 (such as shown) using any type of locking feature, or it can be permanently affixed to it. Likewise, in some implementations, the moveable support 512 can optionally, itself, serve as the depth stop feature 508 of the cutter section 502 by, for example, using any conventional locking mechanism such as a twist lock, catch, locking pin or detent on the shaft 516 and/or moveable support 512. In normal operation, or when not locked (if such optional feature is available), as will be described below, the moveable support 512 facilitates manipulation of a repair patch.

In general, a kit constructed according to the teachings herein, will include one or more lesion sizers and multiple specific cutting tools that individually correspond to each of the sets of markings on the associated lesion sizer 200, 400, in a sterile package. Alternatively, as will be described herein, each of the cutting tools in some variant kits may also serve as a lesion sizer (i.e., they will physically be one and the same unit). The use of the example cutting tool 500 in the process of FIG. 2 is as follows.

Once the lesion sizer 200, 400 has been used to mark an appropriate size and shaped area around the articular cartilage lesion to be repaired, a specific cutting tool corresponding to the size and shape of the particular set of markings on the lesion sizer 200, 400 is selected. Between Panels "C" and "D" of FIG. 2, the surgeon aligns and abuts the periphery of the cutter section 502 with the markings 204 on the cartilage and applies pressure normal to the cutting edge 506, which causes the cutting edge 506 to cut through the cartilage surrounding the cartilage lesion. When either the optional depth stop feature is reached or the surgeon feels resistance indicative of having hit the subchondral bone, the surgeon then removes the cutting tool 500 from the site and prepares the site by removing the cartilage within the cut area as described in connection with FIG. 2.

With this variant, the process of Panel "E" of FIG. 2 would not occur. Rather, the surgeon would merely place the cutting tool 500 on top of the repair patch material 208 and apply pressure to the handle to cause a repair patch 212 to be cut out. By bringing the movable support 512 into contact with the repair patch 512, the repair patch 212 will adhere to the underside of the moveable support 512 allowing it to be removed from the remainder of the repair patch material 208 and transported to the prepared repair site where the periphery of the cutter section 502 will again be aligned with the prepared site. Then, the movable support will be depressed to place the repair patch 212 into the site and, once placed, the moveable support 512 can be removed by, for example, sliding the movable support 512 and cutting tool 500 laterally to break the adhesion, or displacing the repair patch 212 from, the movable support 512 using, for example, forceps, tweezers, a scalpel or other instrument.

Figure 6:
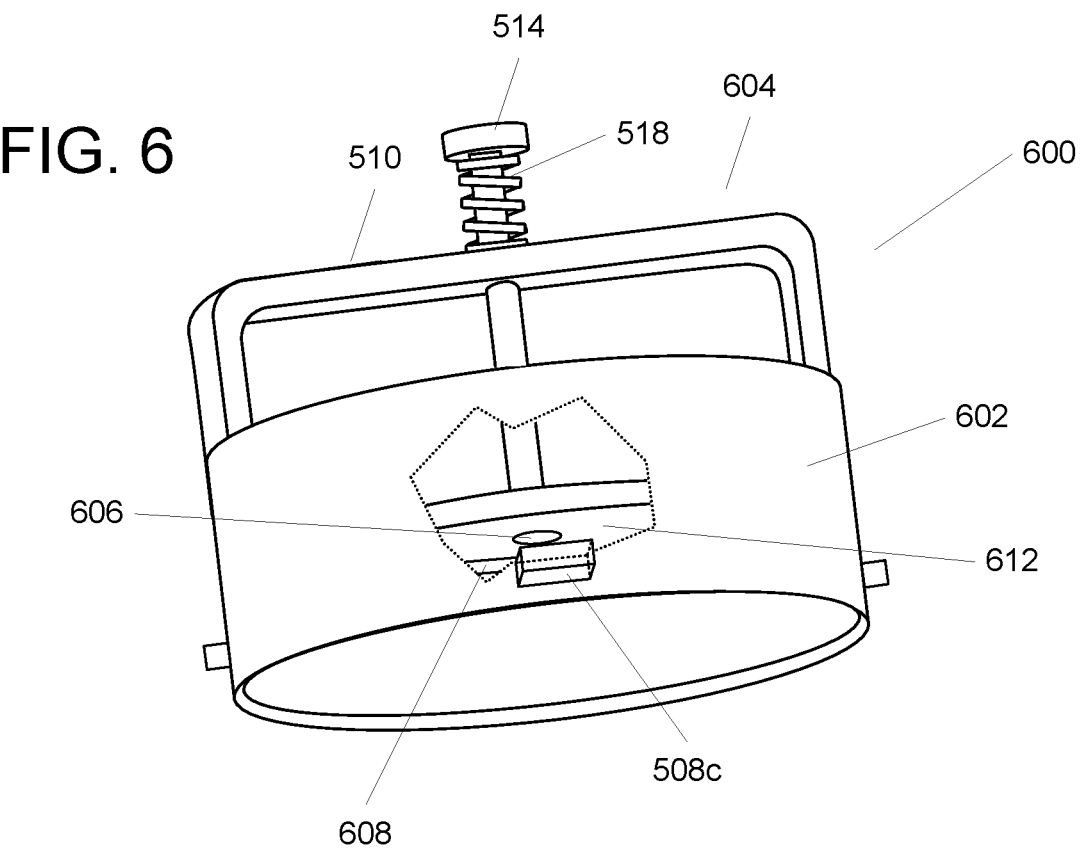
FIG. 6 illustrates, in simplified form, an alternative variant cutting tool that is similar to the cutting tool of FIG. 5.

FIG. 6 illustrates, in simplified form, an alternative variant cutting tool 600 that is similar to the cutting tool 500 of FIG. 5 except that the cutter section 602 and manipulator section 604 are permanently affixed together. In addition, the cutting tool 600 includes an external depth stop feature 508c. In addition, although less visible in this view, the movable support 612 includes one or more internal registration features 606, in the form of holes, that can be used to align the cutting tool 600 with marks applied to underlying cartilage using a lesion sizer 200, 400. In addition, this variant cutting tool 600 further includes openings 608 that provide greater visibility of the repair site for the surgeon during alignment over a lesion-containing cartilage site and can also assist with displacing the repair patch 212 from the movable support 512 at the repair site. The openings 608 can take any form or shape, the only requirement being that the movable support 512 has enough surface area to reliably ensure adhesion of the repair patch 212 to it between cutting and placement. Alternatively, in lieu of openings, the movable support 512 can be transparent or translucent, in whole or part.

Figure 7:
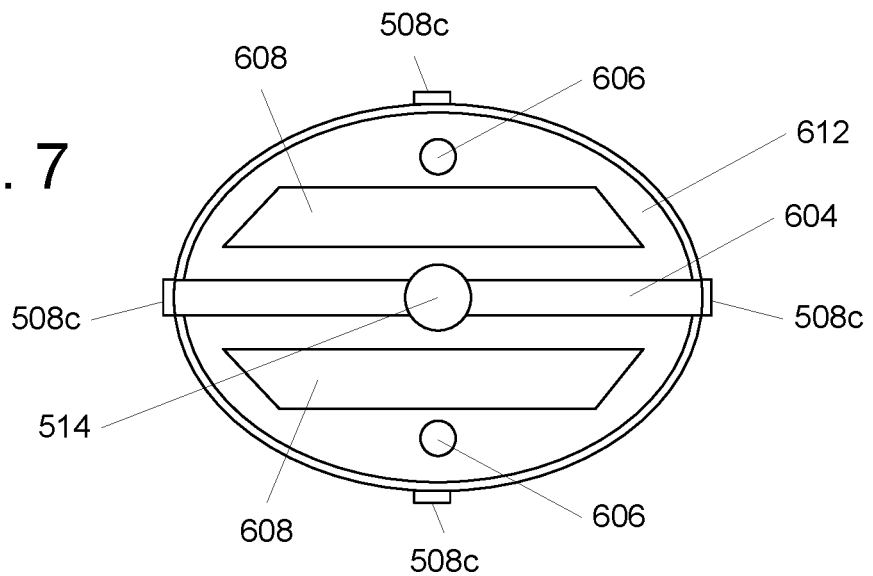
FIG. 7 illustrates, in simplified form, a top down view of the cutting tool of FIG. 6.

FIG. 7 illustrates, in simplified form, a top down view (i.e., in the direction of arrow "X") of the cutting tool 600 of FIG. 6 to better illustrate the internal registration features 606 and openings 608.

Figure 8:
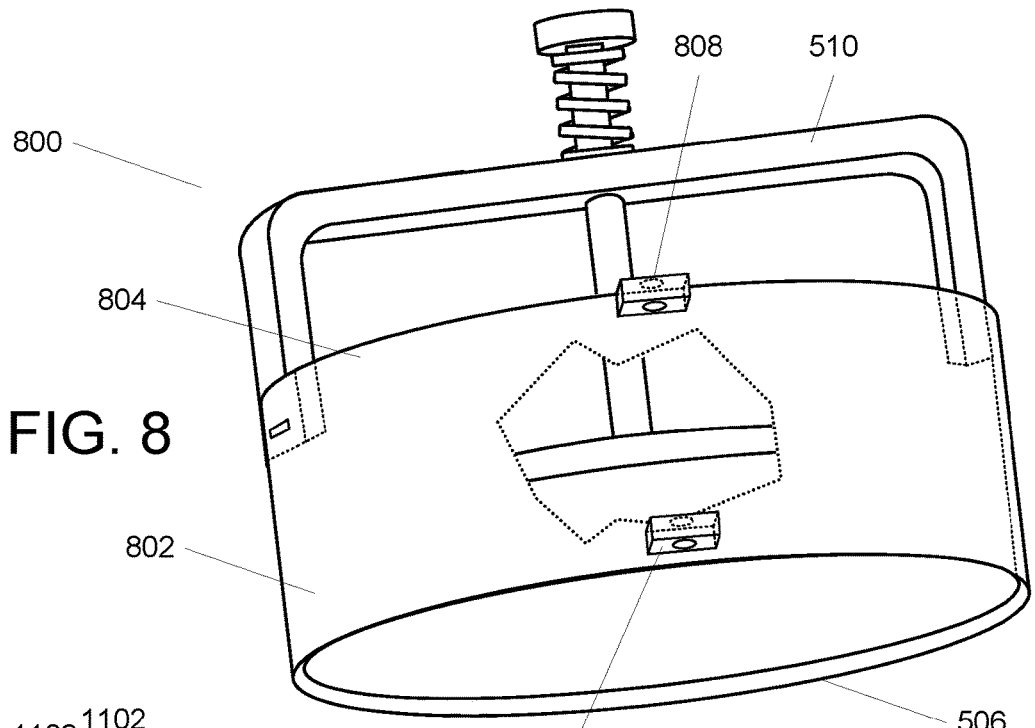
FIG. 8 illustrates, in simplified form, a further alternative example implementation of a cutting tool with a removable handle.

FIG. 8 illustrates, in simplified form, a further alternative example implementation of a cutting tool 800 with a removable handle 504 similar to that described in connection with FIG. 5 above except that, with this implementation, the cutting tool is symmetrical about at least one axis, and ideally two orthogonal axes, and the cutter section 802, on the side 804 opposite the cutting edge 506, when the handle 504 is removed, can act as a lesion sizer 806. In that regard, as shown, the cutter section 802 includes a registration feature 808 (e.g., a protrusion with a through-hole) on the outside of the side 804 of the cutter section 802 that can be used to mark cartilage so that mark can be used to align the corresponding combined depth stop 508d and registration element on the side with the cutting edge 506. It should be further noted that with this type of implementation, the side 804 should ideally be flared outward slightly, to account for the marker pint thickness if marking will be done using the interior of the periphery of the lesion sizer side or flared inward slightly if the marking will be done using the exterior of the lesion sizer side.

Figure 9:
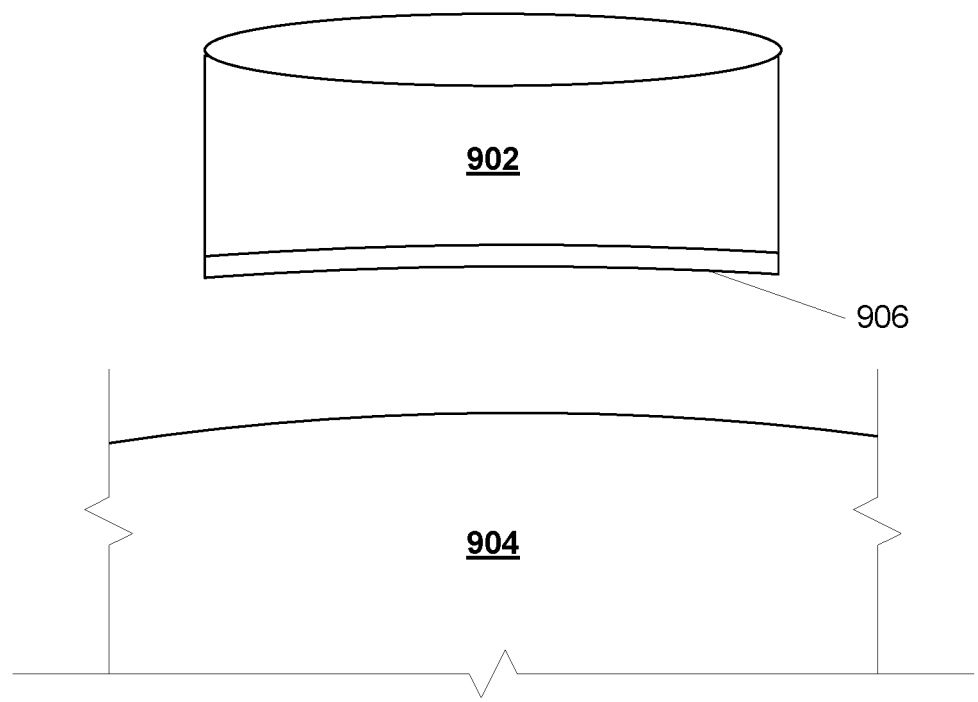
FIG. 9 illustrates, in simplified form, an example cutter section similar to the cutter section of FIG. 5 except that the cutting edge is curved.

Additionally, with many implementations, the cutting edge will be shaped so as to conform to the curvature of the underlying cartilage of the lesion site. FIG. 9 illustrates, in simplified form, an example cutter section 902 similar to the cutter section 502 of FIG. 5 except that the cutting edge 906 is curved to correspond to the curvature of the, for example, the cartilage on a femoral joint ball 904 (only part of which is shown). In such a case, it is contemplated that some kits containing implementations constructed according to the teachings herein may also include a form or "buck" that corresponds to the curvature of a cutter section (e.g., cutter section 902) or the intended repair site over which repair patch material can be draped. In this way, repair patches can be cut to closely match the repair site.

Figure 10:
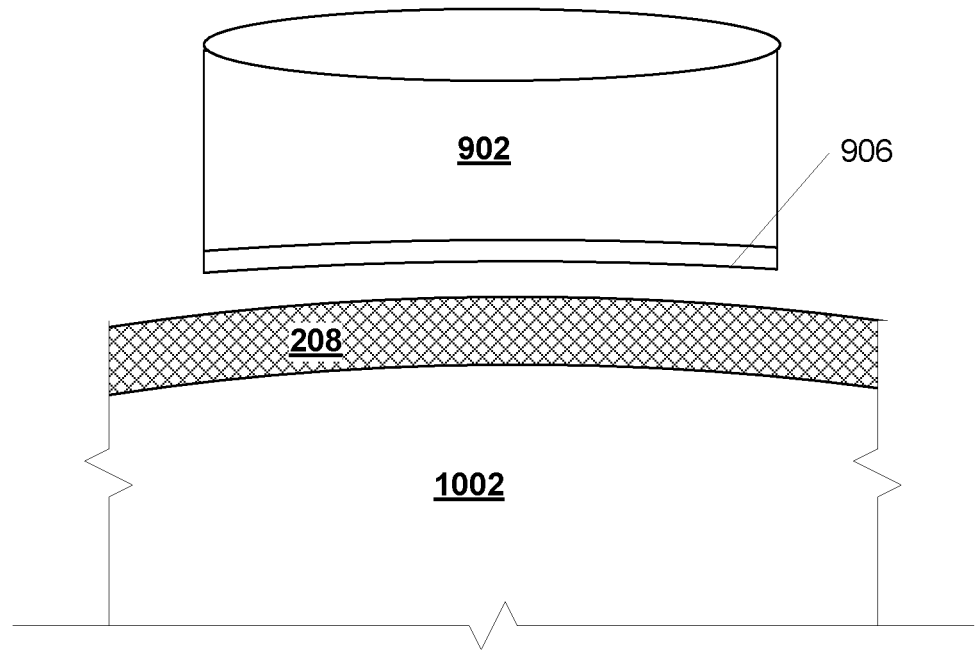
FIG. 10 illustrates, in simplified form, an example cutter section about to cut repair patch material that has been draped over a form or buck that closely corresponds to the curvature of the femoral joint ball.

FIG. 10 illustrates, in simplified form, an example cutter section 902 about to cut repair patch material 208 that has been draped over a form or buck 1002 that closely corresponds to the curvature of the femoral joint ball 904.

Figure 11A:
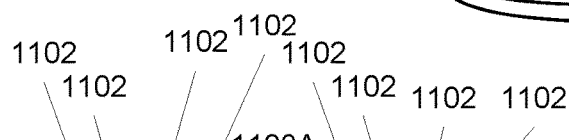
FIGS. 11A-11C illustrate, in simplified form, the outlines of different sized sets of lesion sizers and/or cutting sections of cutting tools as described herein.
Figure 11B:
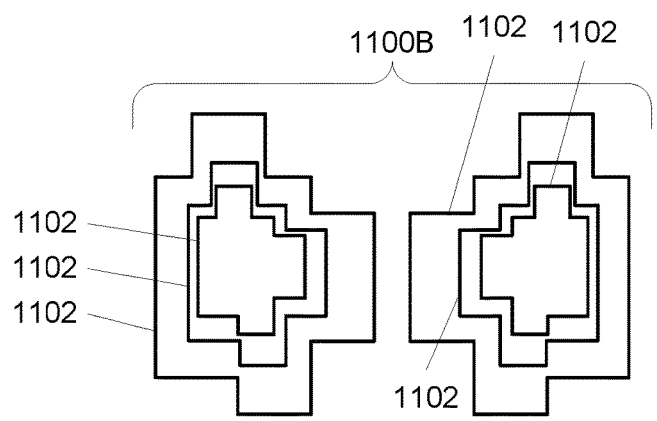
Figure 11C:
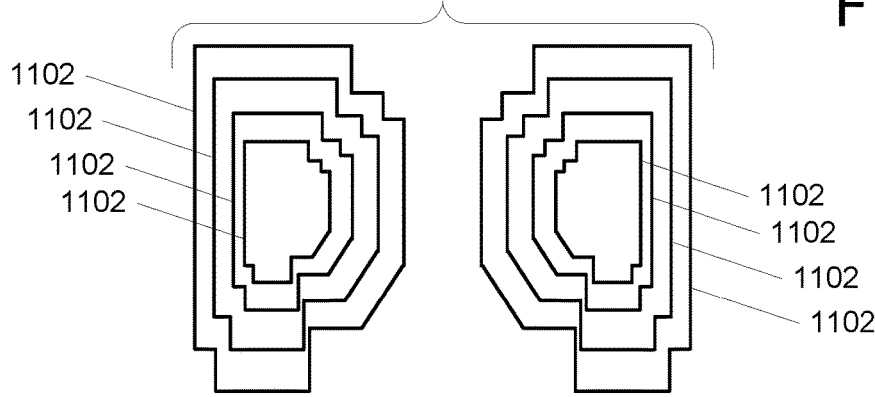

It should now be appreciated that having one or more sets of multiple cutting tools or cutting tools with integral "lesion sizers" allow the surgeon to overlie a cartilage defect to identify the appropriate (peripheral and curvature) shape (inclusive of size) that minimizes the amount of healthy cartilage that needs to be removed, and also ensures highly accurate correspondence between the prepared repair site and the intended cartilage repair patch. Moreover, the tools can also or alternatively be of different shapes to match potential repairable cartilage lesions in any joint in the body. For example, the lesion sizers and/or cutting sections of cutting tools constructed as described herein may be circular, rectangular, ovoid or any other desired closed geometric shape to encompass potential cartilage lesions. For example, FIGS. 11A-11C illustrate, in simplified form, the outlines 1102 of different sized sets 1100A, 1100B, 1100C of lesion sizers and/or cutting sections of cutting tools that substantially correspond to the common lesion areas 304, 306, 308 identified in connection with FIG. 3 and their corresponding mirror images (to account for left side and right side fibular knee joints).

Thus, it should be appreciated that, advantageously, the cutting section of a cutting tool as described herein can have any desired closed geometric shape and the cutting edge can have any (or no) appropriate curvature.

Finally, it should be noted that, for some implementations, the host joint surface need not necessarily be physically marked, for example where techniques such as augmented reality is used. In such a case, a fixed point is selected on the body and a virtual image of the shape appears on a viewing screen for the surgeon, as if it had been drawn on the body. The use a virtual image is particularly useful for arthroscopic techniques, where the virtual image is shown on a computer monitor or display to guide the cartilage removal.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A tool for use in repairing joint articular cartilage lesions, the tool comprising:
   A) a first non-trephine cutting tool having
      i) a closed geometric peripheral shape and a cutting edge, and
      ii) the cutting edge is sufficiently sharp to cut, by the application of force normal to the cutting edge, through
         a) cartilage surrounding a joint articular cartilage lesion from a repair site while having insubstantial effect on subchondral bone underlying the cartilage surrounding the joint articular cartilage lesion cartilage being cut, and
         b) a cartilage repair patch;
   B) a handle comprising at least two arms, a first of the at least two arms being coupled to a first location of the closed geometric peripheral shape and a second of the at least two arms being coupled to a second location of the closed geometric peripheral shape, wherein the first and second locations are spaced apart from each other;

C) a repair patch support, biased relative to the at least two arms in a direction towards the at least two arms and away from the cutting edge, and associated with the first cutting tool which will support a specific cartilage repair patch that was cut using the first cutting tool, and will assist in one or more of transfer to the repair site, or proper placement at the repair site, of a specific cartilage repair patch cut using the first cutting tool.

2. The tool of claim 1, wherein the closed geometric peripheral shape is non-circular.

3. The tool of claim 1, wherein the closed geometric peripheral shape closely, and singularly, encompasses an area corresponding to a typical joint articular cartilage lesion.

4. The tool of claim 1, wherein the first non-trephine cutting tool includes a depth stop feature.

5. The tool of claim 1, wherein the first non-trephine cutting tool includes a lesion sizing element made of translucent material.

6. The tool of claim 5, wherein the closed geometric peripheral shape of the first non-trephine cutting tool defines a plane that is symmetrical about both of two axes that are at right angles to each other and the lesion sizing element is on a side of the first non-trephine cutting tool that is opposite the cutting edge.

7. The tool of claim 1, wherein the cutting edge of the first non-trephine cutting tool has a curvature that corresponds to curvature of the subchondral bone underlying the joint articular cartilage lesion.

8. A tool for use in joint articular cartilage repair comprising:
   a non-trephine cutting tool, having
      i) a handle having at least two arms, the handle being coupled to a movable support via a rod positioned between the at least two arms, the movable support being configured to assist in one or more of transfer to a repair site, or proper placement at the repair site, of a specific cartilage repair patch cut using the non-trephine cutting tool; and
      ii) a cutter section, coupled to the handle, the cutter section having a closed geometric peripheral shape sized to surround a lesion in cartilage of an articular joint, the cutter section having a cutting edge that is sufficiently sharp to cut, by the application of force normal to the cutting edge, through
         a) cartilage surrounding a joint articular cartilage lesion from a repair site while having insubstantial effect on subchondral bone underlying the cartilage surrounding the joint articular cartilage lesion cartilage being cut, and
         b) a cartilage repair patch;
   wherein, the movable support has a peripheral shape that fits within, and closely corresponds to, the closed geometric peripheral shape of the cutter section and is biased relative to the at least two arms in a direction towards the at least two arms and away from the cutting edge.

9. The tool of claim 8, wherein the movable support is transparent.

10. The tool of claim 8, wherein the movable support is translucent.

11. The tool of claim 8, wherein the movable support includes at least one opening therethrough.

12. The tool of claim 8, wherein the movable support is coupled to the handle via a shaft.

13. The tool of claim 8, wherein the handle is removably attachable to the cutter section.

14. The tool of claim 8, wherein the handle is affixed to the cutter section.

15. The tool of claim 8, wherein the cutting edge is curved.

* * * * *